United States Patent
Halverson (10) Patent No.: US 11,813,178 B2
(45) Date of Patent: Nov. 14, 2023

(54) DEPLOYABLE RAMPED NOSE FOR IMPLANTABLE MEDICAL DEVICES

(71) Applicant: Nexus Spine, LLC, Salt Lake City, UT (US)

(72) Inventor: Peter Halverson, Draper, UT (US)

(73) Assignee: Nexus Spine, LLC, Salt Lake City, UT (US)

( * ) Notice: Subject to any disclaimer, the term of this patent is extended or adjusted under 35 U.S.C. 154(b) by 0 days.

(21) Appl. No.: 17/177,073

(22) Filed: Feb. 16, 2021

(65) Prior Publication Data

US 2021/0251775 A1 Aug. 19, 2021

Related U.S. Application Data

(60) Provisional application No. 62/975,922, filed on Feb. 13, 2020.

(51) Int. Cl.
*A61F 2/44* (2006.01)
*A61F 2/46* (2006.01)
(Continued)

(52) U.S. Cl.
CPC .......... *A61F 2/4611* (2013.01); *A61B 17/025* (2013.01); *A61F 2/442* (2013.01);
(Continued)

(58) Field of Classification Search
CPC .................. A61F 2/442; A61F 2/4455; A61F 2002/4615; A61F 2/447; A61F 2/4611
See application file for complete search history.

(56) References Cited

U.S. PATENT DOCUMENTS 10,105,238 B2 * 10/2018 Koch .................. A61F 2/44
10,687,961 B1 * 6/2020 Abdelgany ............ A61F 2/447
(Continued)

FOREIGN PATENT DOCUMENTS

WO 2008070863 A2 6/2008
WO 2009092960 A2 7/2009
(Continued)

OTHER PUBLICATIONS

International Search Report and Written Opinion from corresponding PCT App. No. PCT/US2021/018265.

*Primary Examiner* — Eduardo C Robert
*Assistant Examiner* — Steven J Cotroneo
(74) *Attorney, Agent, or Firm* — Bryant J. Keller; Kirton McConkie (57) ABSTRACT

A surgical implant includes a deployable, retractable, or removable ramped nose. During insertion of the implant, the ramped nose is deployed such that the ramped nose can serve to distract a space into which the implant is inserted. At some point during or after insertion, the ramped nose can be collapsed and removed or retracted so that it does not extend beyond the space into which the implant is inserted, while the implant extends at full height throughout the space into which the implant is inserted. The implant includes an implant body having a deployable ramped nose adapted to selectively extend from the body and transition from a first height proximate the implant body to a second, shorter, height distal from the implant body. The deployable ramped nose is adapted to distract an implant site upon insertion of the implantable medical device.

20 Claims, 9 Drawing Sheets

(51) Int. Cl.
*A61B 17/02* (2006.01)
*A61F 2/30* (2006.01)

(52) U.S. Cl.
CPC ............. *A61B 2017/0256* (2013.01); *A61F 2002/30266* (2013.01); *A61F 2002/4615* (2013.01); *A61F 2002/4627* (2013.01)

(56) References Cited

U.S. PATENT DOCUMENTS

| | | | | |
|---|---|---|---|---|
| 2014/0194991 | A1* | 7/2014 | Jimenez | A61F 2/442 623/17.15 |
| 2014/0277477 | A1 | 9/2014 | Malandain | |
| 2015/0018954 | A1* | 1/2015 | Loebl | A61F 2/447 623/17.16 |
| 2016/0022434 | A1* | 1/2016 | Robinson | A61F 2/4611 623/17.16 |
| 2016/0030190 | A1* | 2/2016 | Robinson | A61F 2/447 623/17.16 |
| 2018/0344473 | A1* | 12/2018 | Baynham | A61F 2/442 |
| 2019/0269521 | A1 | 9/2019 | Shoshtaev | |
| 2021/0068973 | A1* | 3/2021 | McLuen | A61F 2/30 |
| 2021/0137695 | A1* | 5/2021 | Huang | A61F 2/4455 |
| 2021/0196469 | A1* | 7/2021 | Caratsch | A61F 2/4611 |
| 2022/0175547 | A1* | 6/2022 | Fresneau | A61F 2/447 |

FOREIGN PATENT DOCUMENTS

| | | |
|---|---|---|
| WO | 2009144562 A1 | 12/2009 |
| WO | 2011007240 A1 | 1/2011 |

* cited by examiner

DEPLOYABLE RAMPED NOSE FOR IMPLANTABLE MEDICAL DEVICES

CROSS-REFERENCE TO RELATED APPLICATIONS

This application claims the benefit of U.S. Provisional Application No. 62/975,922, filed Feb. 13, 2020, which is incorporated herein by reference in its entirety.

BACKGROUND OF THE INVENTION

1. Field of the Invention

The present invention relates to implantable medical devices, and more particularly to deployable ramped noses to facilitate device insertion.

2. Background and Related Art

A diseased or damaged human spinal disc can collapse, losing most if not all of its original height. At times, surgical intervention is used to attempt to restore the disc space (or disc spaces in the case of collapse of multiple discs) to a healthy height. Various surgical methods are used in attempts to restore healthy disc height. Some instruments, such as screw neck distractors, lamina spreaders, and the like, provide for temporary distraction of the disc space, but available instruments can complicate the surgery, create bulk in the surgical wound, and can be difficult to operate.

In some instances, an intervertebral surgical spacer is used to more-permanently distract the disc space and to attempt to restore a healthy height to the disc space. Unfortunately, there are difficulties in effectively using intervertebral surgical spacers. It can be difficult to temporarily distract the disc space long enough to insert the intervertebral surgical spacer. In particular, there may be insufficient room to access the vertebra and temporarily distract the disc space and also insert a full-height surgical spacer.

Figure 1:
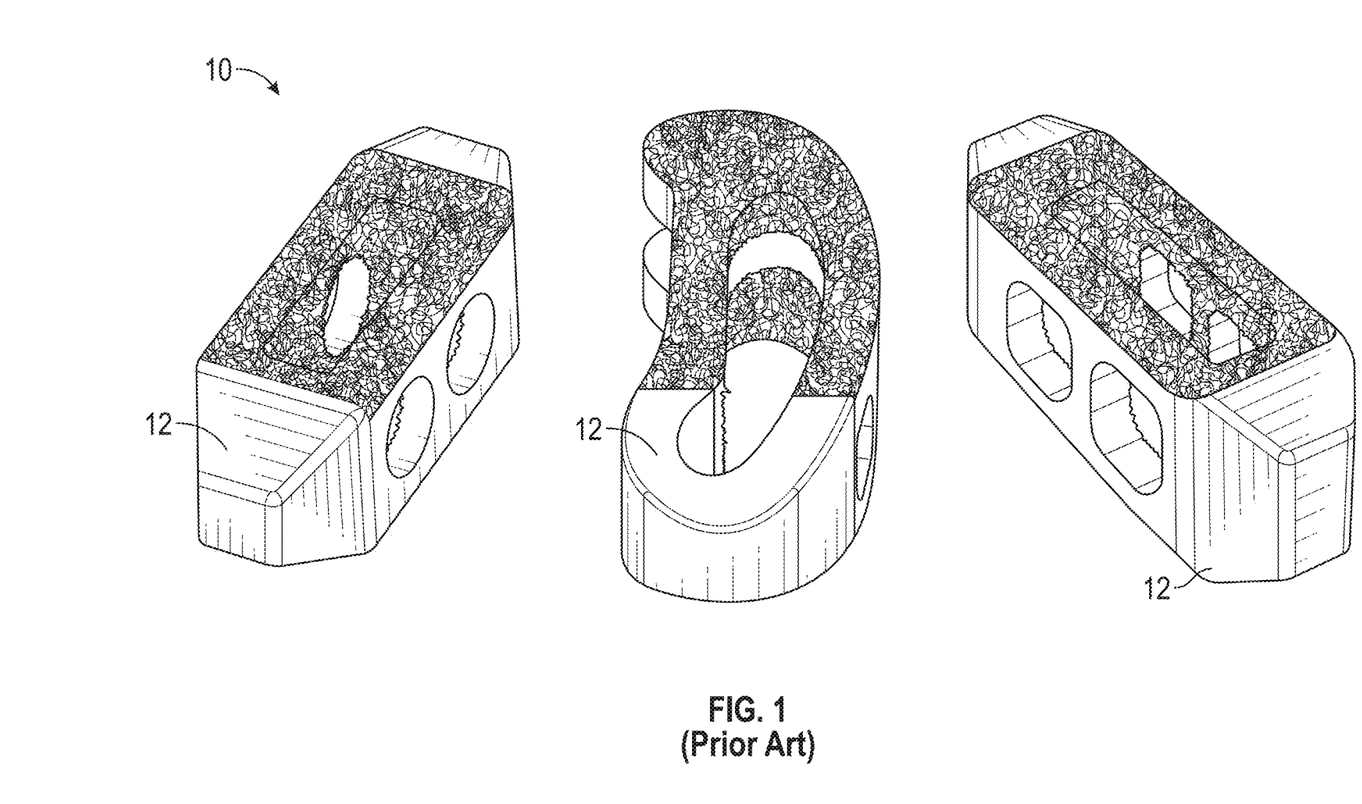
FIG. 1 shows a perspective view of representative prior-art surgical spacers.
Figure 2:
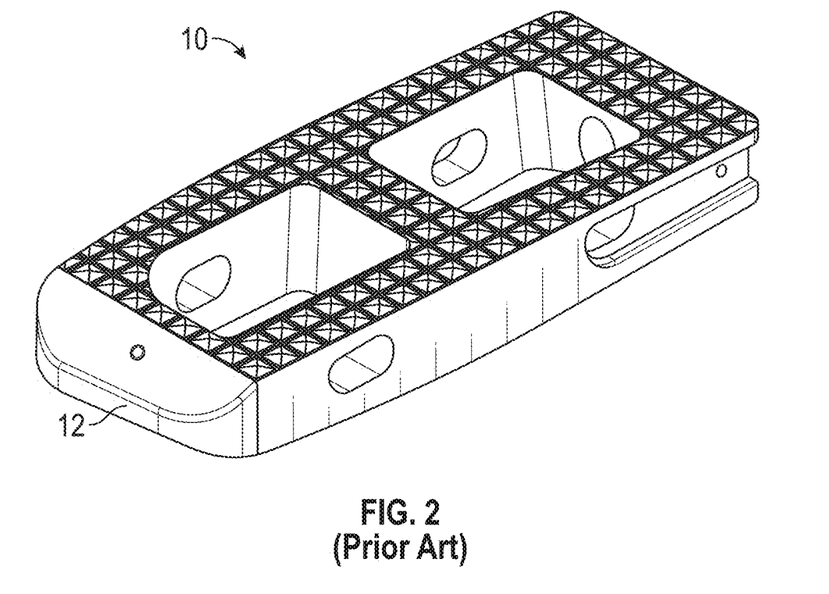
FIG. 2 shows a prior-art surgical spacer.

To address this deficiency, some prior-art surgical spacers 10 are provided with a ramped nose 12, as illustrated in FIGS. 1 and 2. The ramped nose 12 has an initial height that is less than the full height of the surgical spacer 10, such that separate distraction of the intervertebral space is not necessary or is less necessary; instead, the shorter portion of the ramped nose 12 is pushed into the intervertebral space, and as the surgical spacer 10 is pushed into the intervertebral space, the sloped leading edges of the ramped nose 12 of the surgical spacer 10 serve to distract the vertebra, allowing the surgical spacer 10 to enter the intervertebral space.

Unfortunately, use of surgical spacers 10 with such ramped noses 12 is subject to at least one of two problems due to the presence of the ramped nose 12. Because the ramped nose portion of the implant is not the desired full healthy height of the disc space, at least one of two tradeoffs is required. In some circumstances, the surgical spacer 10 is sized to be disposed entirely within the intervertebral (disc) space. For the surgical spacer 10 to have the ramped nose 12, the surgical spacer 10 thus contacts the adjacent vertebra on less than the entire intervertebral surfaces thereof (or on less surface than a full-height surgical spacer would). In such circumstances, because the vertebral load is spread over a smaller area, there is an increased risk of subsidence. When subsidence occurs, the restored healthy height can be lost, resulting in recurrence of pain and other issues.

Furthermore, even if subsidence does not occur, placement of the surgical spacer 10 entirely within the intervertebral space may result in uneven height restoration of the disc space. This uneven height restoration is due to the ramped nose portion of the implant, which thus lacks the full-height support on one side of the intervertebral space. This uneven height restoration can alter the relative rotation of the adjacent vertebral bodies, inducing an undesirable spinal curve.

Because the occurrence of subsidence and the extent thereof can be difficult to predict, the surgeon cannot use a larger-thickness surgical spacer even if he or she wanted to. Additionally, if a larger-thickness surgical spacer were used, the increased distraction prior to subsidence could lead to unwanted pain. Accordingly, for these reasons, the use of surgical spacers 10 with ramped noses 12 fitting entirely within the intervertebral space is less than ideal.

Figure 3:
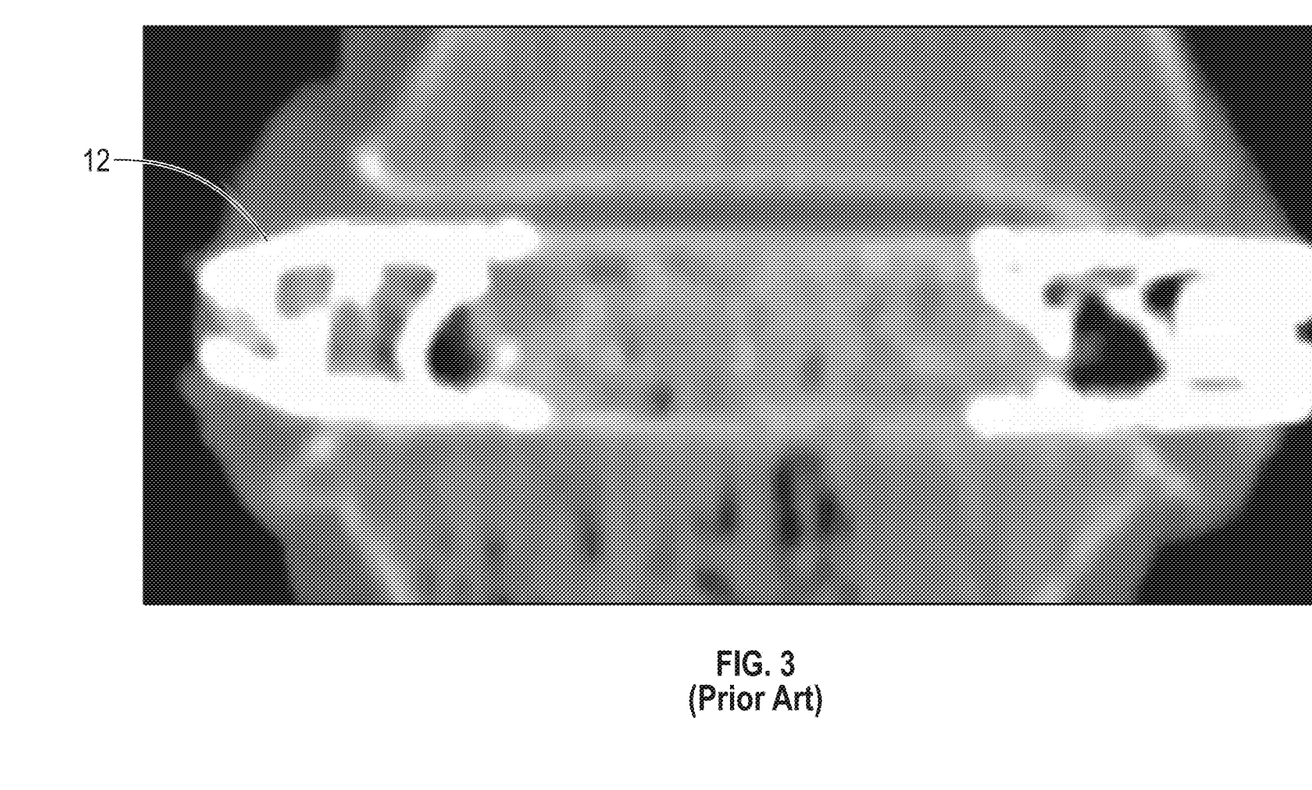
FIG. 3 shows a radiograph of a prior-art surgical spacer in situ.

Accordingly, there has been some effort to use surgical spacers 10 that are larger than the intervertebral space, such that the ramped nose 12 protrudes beyond the intervertebral space on one side after insertion and placement of the surgical spacer 10, as illustrated in the radiograph shown in FIG. 3. The use of such ramped-nose implants, however, leaving portions of the implants proud of the disc space, places extraspinal anatomical structures at risk of damage or inflammation. Accordingly, patients receiving such surgical spacers 10 may find that their pain is not relieved as expected from the procedure, or that other complications arise.

BRIEF SUMMARY OF THE INVENTION

Implementation of the invention provides an implantable medical device that addresses the deficiencies described in the background. In particular, implementation of the invention provides an implantable medical device such as a surgical spacer, a vertebral spacer, a spinal implant, or an intervertebral spacer that includes a deployable, retractable, or removable ramped nose. During insertion of the implant, the ramped nose is deployed such that the ramped nose can serve to distract a space into which the implant is inserted. At some point during or after insertion, the ramped nose can be collapsed and removed or retracted so that it does not extend beyond the space into which the implant is inserted, while the implant extends at full height throughout the space into which the implant is inserted.

According to implementations of the invention, an implantable medical device includes an implant body having a length and a height and a deployable ramped nose adapted to selectively extend from the body and transition from a first height proximate the implant body to a second, shorter, height distal from the implant body. In some embodiments, the deployable ramped nose is adapted to distract an implant site upon insertion of the implantable medical device. In some embodiments, the deployable ramped nose is in a deployed state during initial insertion of the implantable medical device, and is retracted within the implant body after initial insertion of the implantable medical device. In some embodiments, the deployable ramped nose is retracted before the implantable medical device is fully inserted, whereby the deployable ramped nose does not extend into a space beyond a targeted insertion location of the implant body during insertion of the implantable medical device.

In some embodiments, the deployable ramped nose includes a pair of ramps hingedly connected to an elongate member proximate a distal end of the deployable ramped nose. In some embodiments, proximal ends of the pair of ramps rest on and engage with a pair of shelves of the implant body to prevent collapsing of the ramps. In some embodiments, the ramps are biased to a collapsed state such that when the deployable ramped nose is advanced while the implant body is retained against advancing, the proximal ends of the ramps disengage with the shelves and collapse to a position in which the deployable ramped nose may be withdrawn into the implant body. In some embodiments, the ramps are biased to a collapsed state such that when the deployable ramped nose is advanced while the implant body is retained against advancing, the proximal ends of the ramps disengage with the shelves and collapse to a position in which the deployable ramped nose may be withdrawn through the implant body.

In some embodiments, the implant body forms an intervertebral spacer. In some embodiments, the deployable ramped nose is also adapted to transition from a first thickness proximate the implant body to a second, thinner, thickness distal from the implant body. In some embodiments, the implantable medical device further includes a tool adapted to selectively deploy the deployable ramp nose. In some embodiments, the implantable medical device further includes a tool adapted to selectively collapse and retract the deployable ramp nose.

According to further implementations of the invention, a method for utilizing an implantable medical device having a deployable ramp nose, includes steps of deploying a deployable ramp nose from an implant body of an implantable medical device, inserting the implantable medical device, with the deployable ramp nose leading, into an implant location, until the implant body is at least partially within the implant location, and retracting the deployable ramp nose whereby the implantable medical device does not extend beyond the implant location but extends a full desired height of the implant body within the implant location.

In some embodiments, the deployable ramp nose is retracted before the implant body is fully within the implant location. In some embodiments, the deployable ramp nose is retracted only after the implant body is fully within the implant location. In some embodiments, during the step of inserting the implantable medical device, the deployable ramp nose distracts the implant location to make room for the implant body.

In some embodiments, the method further includes collapsing the deployable ramp nose before retracting the deployable ramp nose. In some embodiments, the method further includes removing the deployable ramp nose from the implant body after retracting the deployable ramp nose.

In some embodiments, the method further includes disengaging a member that secures the deployable ramped nose against collapse and allowing the deployable ramped nose to collapse before retracting the deployable ramped nose. In some embodiments, a combination insertion/retraction tool is used to apply an advancing force to advance the implantable medical device into the implant location and to cause the deployable ramp nose to retract.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide an implantable medical device that addresses the deficiencies described in the background. In particular, embodiments of the invention provide an implantable medical device such as a surgical spacer, a vertebral spacer, a spinal implant, or an intervertebral spacer that includes a deployable, retractable, or removable ramped nose. During insertion of the implant, the ramped nose is deployed such that the ramped nose can serve to distract a space into which the implant is inserted. At some point during or after insertion, the ramped nose can be collapsed and removed or retracted so that it does not extend beyond the space into which the implant is inserted, while the implant extends at full height throughout the space into which the implant is inserted.

According to embodiments of the invention, an implantable medical device includes an implant body having a length and a height and a deployable ramped nose adapted to selectively extend from the body and transition from a first height proximate the implant body to a second, shorter, height distal from the implant body. In some embodiments, the deployable ramped nose is adapted to distract an implant site upon insertion of the implantable medical device. In some embodiments, the deployable ramped nose is in a deployed state during initial insertion of the implantable medical device, and is retracted within the implant body after initial insertion of the implantable medical device. In some embodiments, the deployable ramped nose is retracted before the implantable medical device is fully inserted, whereby the deployable ramped nose does not extend into a space beyond a targeted insertion location of the implant body during insertion of the implantable medical device.

In some embodiments, the deployable ramped nose includes a pair of ramps hingedly connected to an elongate member proximate a distal end of the deployable ramped nose. In some embodiments, proximal ends of the pair of ramps rest on and engage with a pair of shelves of the implant body to prevent collapsing of the ramps. In some embodiments, the ramps are biased to a collapsed state such that when the deployable ramped nose is advanced while the implant body is retained against advancing, the proximal ends of the ramps disengage with the shelves and collapse to a position in which the deployable ramped nose may be withdrawn into the implant body. In some embodiments, the ramps are biased to a collapsed state such that when the deployable ramped nose is advanced while the implant body is retained against advancing, the proximal ends of the ramps disengage with the shelves and collapse to a position in which the deployable ramped nose may be withdrawn through the implant body.

In some embodiments, the implant body forms an intervertebral spacer. In some embodiments, the deployable ramped nose is also adapted to transition from a first thickness proximate the implant body to a second, thinner, thickness distal from the implant body. In some embodiments, the implantable medical device further includes a tool adapted to selectively deploy the deployable ramp nose. In some embodiments, the implantable medical device further includes a tool adapted to selectively collapse and retract the deployable ramp nose.

According to further embodiments of the invention, a method for utilizing an implantable medical device having a deployable ramp nose, includes steps of deploying a deployable ramp nose from an implant body of an implantable medical device, inserting the implantable medical device, with the deployable ramp nose leading, into an implant location, until the implant body is at least partially within the implant location, and retracting the deployable ramp nose whereby the implantable medical device does not extend beyond the implant location but extends a full desired height of the implant body within the implant location.

In some embodiments, the deployable ramp nose is retracted before the implant body is fully within the implant location. In some embodiments, the deployable ramp nose is retracted only after the implant body is fully within the implant location. In some embodiments, during the step of inserting the implantable medical device, the deployable ramp nose distracts the implant location to make room for the implant body.

In some embodiments, the method further includes collapsing the deployable ramp nose before retracting the deployable ramp nose. In some embodiments, the method further includes removing the deployable ramp nose from the implant body after retracting the deployable ramp nose.

In some embodiments, the method further includes disengaging a member that secures the deployable ramped nose against collapse and allowing the deployable ramped nose to collapse before retracting the deployable ramped nose. In some embodiments, a combination insertion/retraction tool is used to apply an advancing force to advance the implantable medical device into the implant location and to cause the deployable ramp nose to retract.

FIGS. 4-8 illustrate views of an illustrative implant 20 in accordance with embodiments of the invention. The illustrative implant 20 or implantable medical device shown in the Figures is simplified for purposes of illustrating the deployable ramped nose or ramp nose features of implants in accordance with embodiments of the invention. Accordingly, the drawings are not intended to be drawn to scale and should not be interpreted as limiting on the scope of the invention, and variations on the relative size or shape of the aspects of implants and implantable medical devices in accordance with embodiments of the invention are embraced within the meaning and scope of the claim set provided herein.

Figure 4:
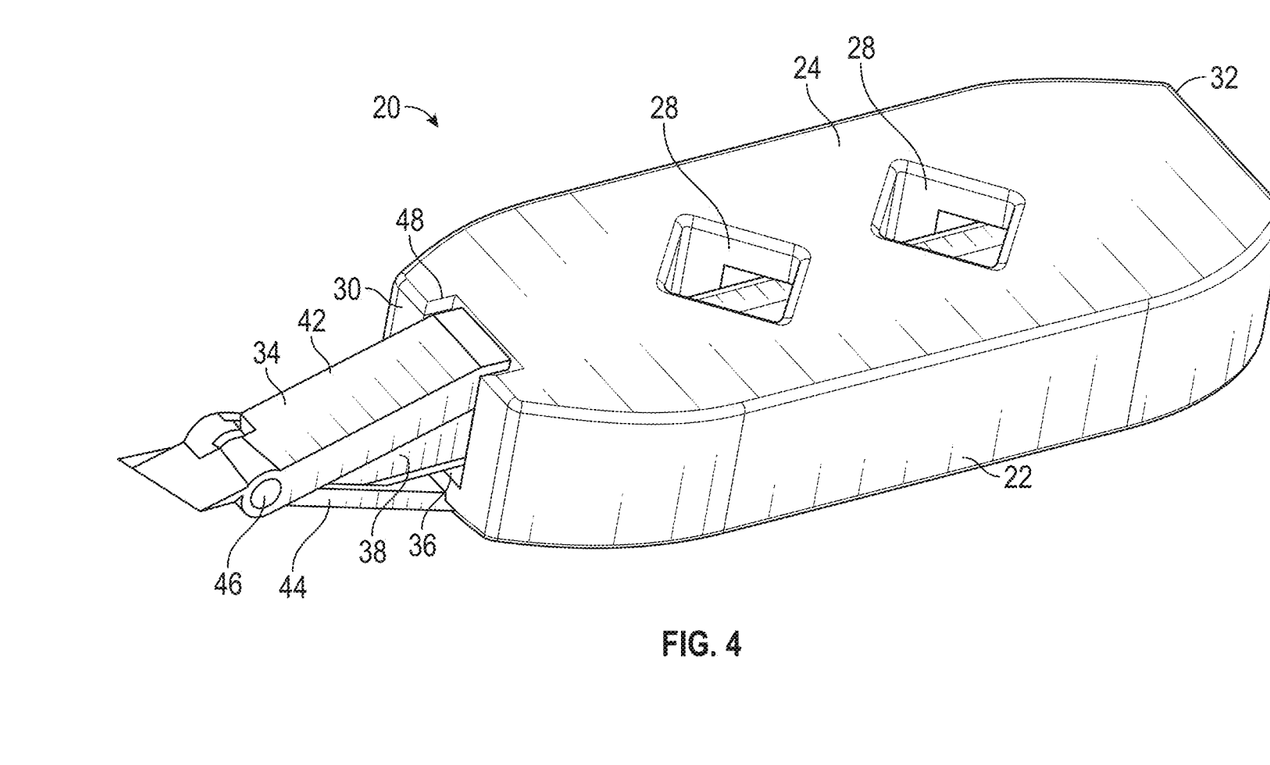
FIG. 4 shows a perspective view of a representative implant with a deployable nose.

In particular, while the implant 20 illustrated in FIGS. 4-8 is shown as having a generally straight configuration in its longitudinal aspect, alternative embodiments of the invention embrace implants having a curved configuration in their longitudinal aspects (see, e.g., the middle surgical spacer 10 of FIG. 1 (curved aspect) vis-à-vis the other surgical spacers 10 of FIG. 1 (straight aspects). Additionally, while the implant 20 of FIG. 4 is depicted as having a generally smooth outer surface, implants in accordance with embodiments of the invention may have a smooth outer surface, a rough, porous outer surface, or a variable outer surface with smooth portions and with porous portions.

Further variations in the exact configuration of the size, shape, exact dimensions, etc. of the implant 20 and on variations of the implant 20 will be readily ascertainable to one of ordinary skill in the art and need not be enumerated in full here. For example, when the implant 20 is intended for use as an intervertebral spacer in the cervical region, its dimensions will be significantly different from the implant 20 when intended for use as an intervertebral spacer in the lumbar region, and one of ordinary skill in the art will be well aware of the size, shape, and dimension variations necessary to account for such varied use. One of ordinary skill in the art, furthermore, will be aware of variations to the implant 20 necessary to account for varying surgical approaches (e.g. DLIF vs. TLIF vs. ALIF vs. PLIF vs. XLIF) and the like.

Accordingly, for all these reasons, the depiction of the implant 20 of FIG. 4 is not intended to depict a final actual implant for use in any particular procedure, but is instead intended to facilitate the discussion herein. The implant 20 is intended to represent any of a variety of implantable medical devices such as surgical spacers, vertebral spacers, intervertebral implants, spinal implants, and the like, and the wording "implant" serves a shorthand reference to any such device. The implant 20 has an implant body 22. The implant body 22 has dimensions selected to allow the implant 20 to provide support at the implant location or implant site, e.g., at an intervertebral space.

Accordingly, the implant body 22 has a height between an upper surface 24 thereof and a lower surface 26 thereof that is selected to provide such support across an entire length of the implant body 22. In some embodiments, the height of the implant body 22 is constant or relatively constant along the length of the implant body 22, while in other embodiments, the height of the implant body 22 varies across the length and/or width of the implant body 22. The variation of height in some embodiments is selected to allow the implant body 22 to conform to the surfaces of bone at the implant location, as is known in the art, and allows stresses to be move-evenly distributed between the implant body 22 and the bone at the implant location.

While not depicted in FIG. 4, the upper surface 24 and the lower surface 26 of some embodiments of the implant body 22 are formed as or provided with a porous structure. The porous structure of such embodiments serves to promote or facilitate bone ingrowth and/or bone ongrowth to the implant body 22, as is known in the art. Additionally, the implant body 22 includes one or more voids 28 formed therein into which a surgeon may optionally place bone graft material (e.g., morcellized/morselized bone such as bone taken from the iliac crest) to encourage bone growth into the void 28 or voids 28 as part of the healing process. In some embodiments, the void 28 or voids 28 extend through the implant body 22 from the upper surface 24 to the lower surface 26.

The implant body 22 has a first end 30 and a second end 32. In the illustrated embodiment, the first end 30 and the second end 32 are spaced on the long axis of the implant body 22. A deployable ramped nose 34 is adapted to be deployed and to extend from the first end of the implant body 22. A channel 36 (most-easily visible in FIG. 8) extends through the implant body 22 from the first end 30 to the second end 32, and provides passage for a ramped nose support 38 and for a manipulating tool 40, as well as for entry and potentially passage of the ramped nose 34 therethrough in a collapsed state, as shown in FIGS. 7-8.

The ramped nose 34 may take a variety of configurations, and may be provided in any configuration that is sufficiently stable and strong to provide distraction of the bone during at least initial insertion of the implant 20 (e.g., until at least a portion of the implant body 22 is sufficiently within the implant location to prevent collapse of the space into which the implant 20 is being inserted). Accordingly, while the ramped nose 34 is shown in one configuration in FIGS. 4-8, it should be understood that any deployable and/or collapsible configuration of a ramped nose is embraced within the scope of the appended claim set. Additionally, while one particular ramp angle of the ramped nose 34 is shown in FIGS. 4-8, other ramp angles are embraced by various embodiments of the invention.

Figure 5:
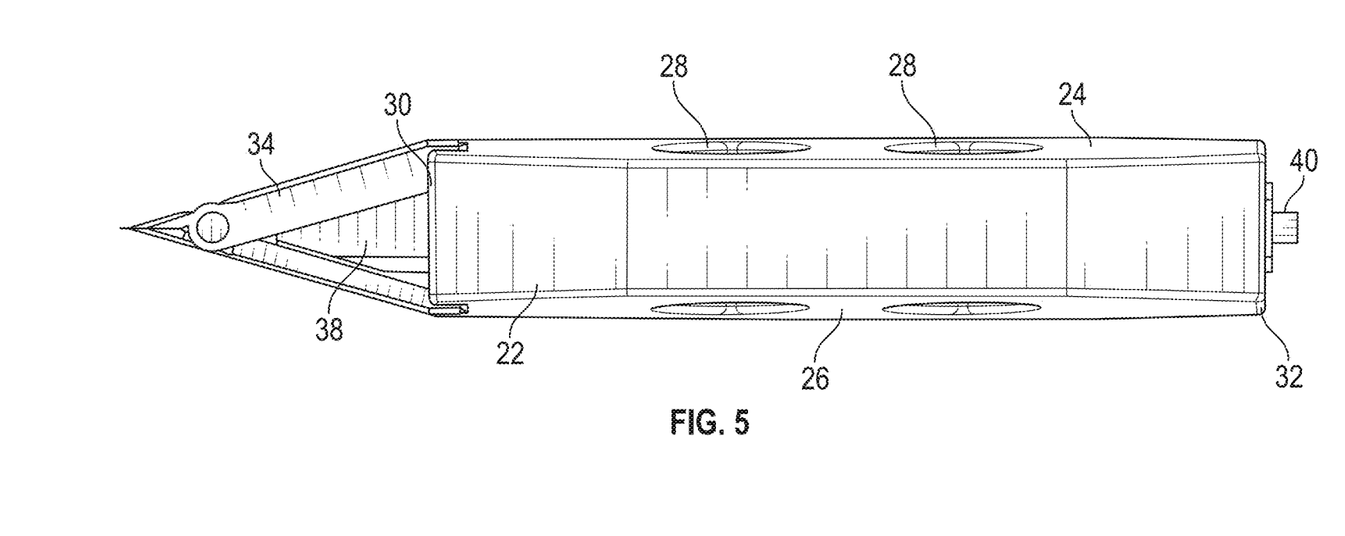
FIG. 5 shows a side view of a representative implant with a deployable nose.
Figure 6:
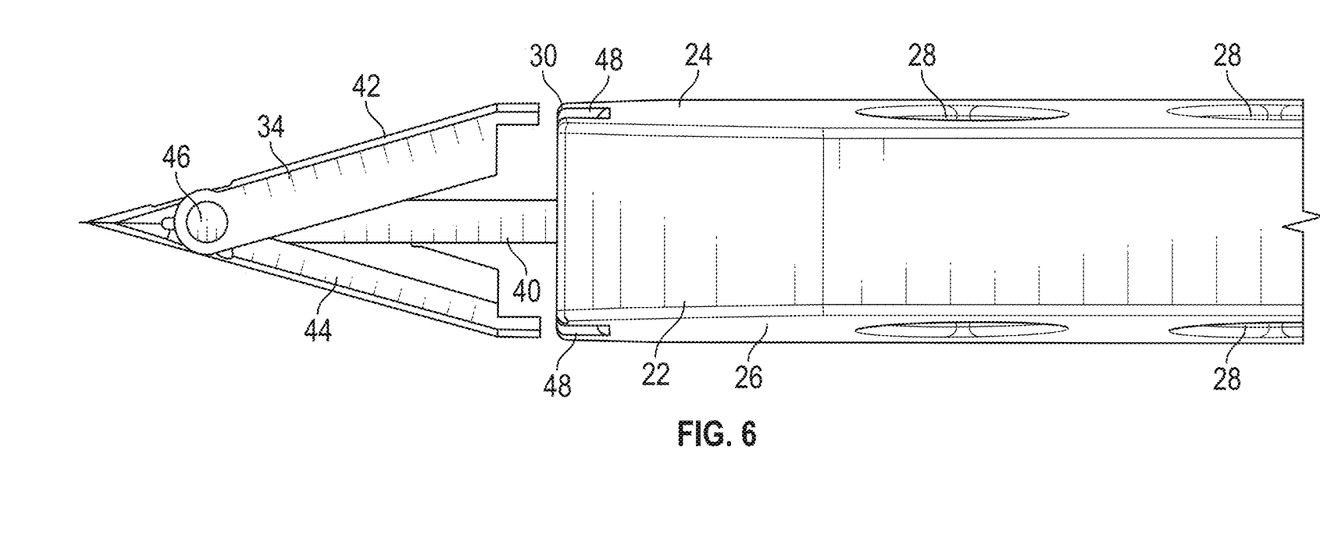
FIG. 6 shows a side view of a representative implant with a deployable nose in a position for deploying/retracting the deployable nose with the deployable nose expanded.
Figure 7:
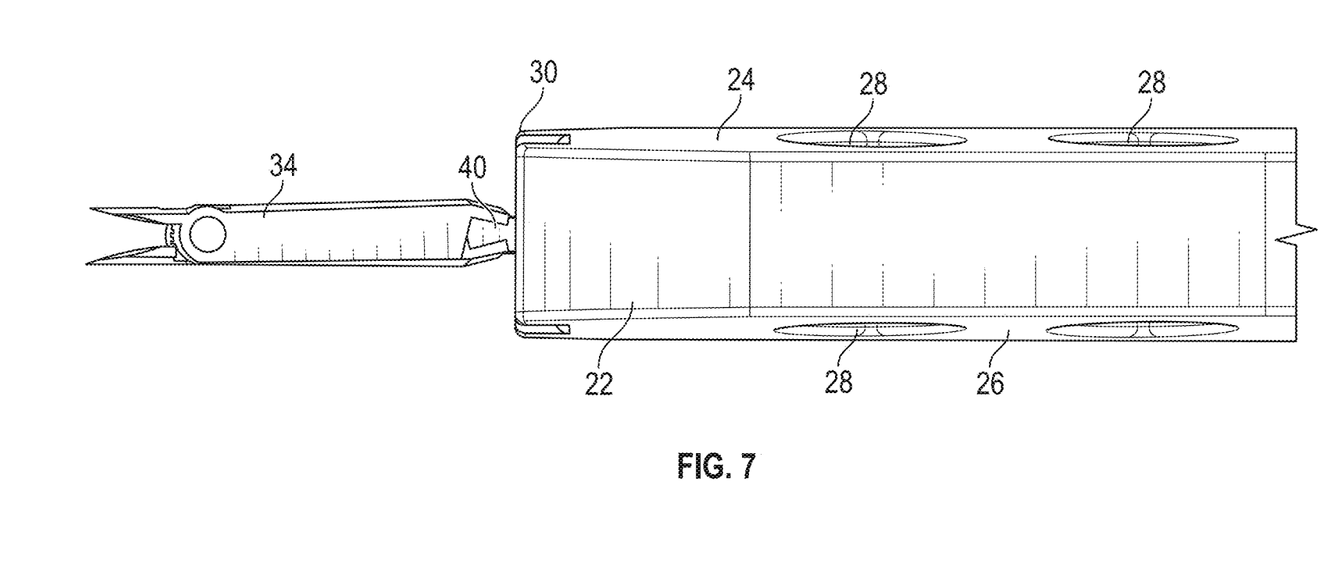
FIG. 7 shows a side view of a representative implant with a deployable nose in a position for deploying/retracting the deployable nose with the deployable nose collapsed.
Figure 8:
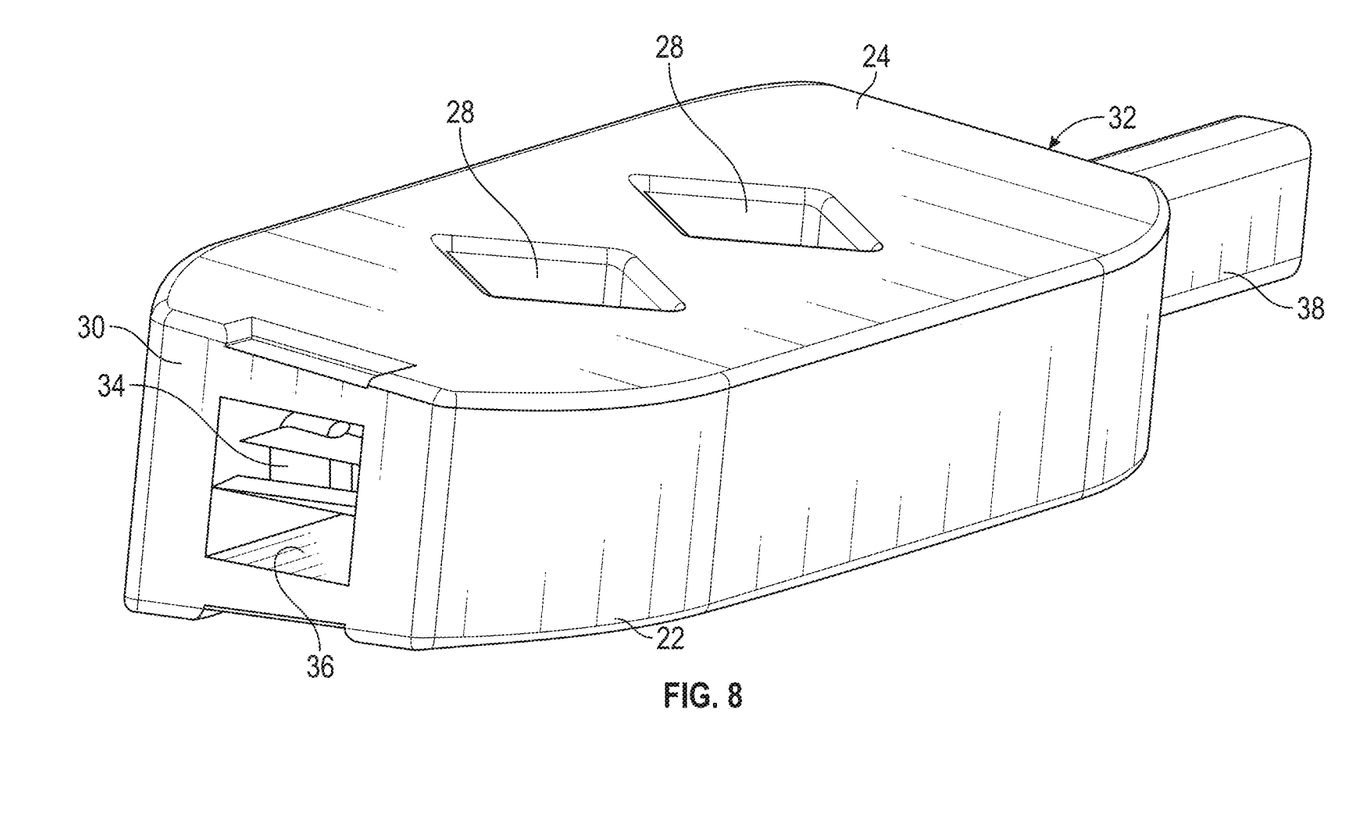
FIG. 8 shows a perspective view of a representative implant with a deployable nose in a retracted position.

In the embodiment illustrated in FIGS. 4-8, the ramped nose 34 is formed as two ramps, an upper ramp 42 and a lower ramp 44 hingedly pinned by a pin member 46. The ramped nose support 38 slides forward/distally in the direction of the first end 30 from the second end 32, thereby forcing proximal ends of the upper ramp 42 and the lower ramp 44 apart as shown in FIGS. 4-5. In some embodiments, when the ramped nose 34 is fully deployed, the proximal ends of the upper ramp 42 and the lower ramp 44 are supported within one or more ramp notches 48 formed in the implant body 22 (see FIG. 4). When the ramped nose support 38 is withdrawn proximally (in the direction of the second end 32), it stops supporting the upper ramp 42 and the lower ramp 44. When the ramped nose 34 is advanced distally slightly, relative to the implant body 22 (as shown in FIG. 6), the upper ramp 42 and the lower ramp 44 separate from the supporting ramp notches 48 and are free to collapse together, as shown in FIG. 7.

In some embodiments, the upper ramp 42 and the lower ramp 44 are biased toward one another, such that when unsupported the ramped nose 34 assumes the collapsed configuration shown in FIG. 7. Such biasing may be achieved, for example, by way of a spring or spring-like member extending between the upper ramp 42 and the lower ramp 44. In some embodiments, a spring or spring-like member is located between the upper ramp 42 and the lower ramp 44 at or distally of the pin member 46. To deploy the ramped nose 34, such biasing is overcome by insertion of the ramped nose support 38 while the ramped nose 34 is in a position similar to that of FIG. 7, thereby forcing the proximal ends of the upper ramp 42 and the lower ramp 44 apart, and then the ramped nose 34 and the ramped nose support 38 are jointly drawn proximally until the proximal ends of the upper ramp 42 and the lower ramp 44 rest in the ramp notches 48. Alternatively, the ramped nose 34 may be deployed manually upon manufacture or by the surgeon prior to insertion of the implant 20.

In any event, the deployed ramped nose 34 serves to distract the implant location (e.g. the vertebral bodies) beginning with a very narrow point at the distal end of the ramped nose 34. As may be seen by comparing the distal end of the ramped nose 34 with the ramped noses of the prior-art devices shown in FIG. 1 and FIG. 2, the ramped nose 34 provides advantages in having a smaller initial profile to ease initial insertion, and because the ramped nose 34 will be withdrawn, it can also have a greater length and gentler slope to facilitate smooth distraction of the implant location during insertion.

In use, once the implant 20 has been inserted sufficiently such that the vertebral bodies (or other bone surrounding the implant location) have been distracted and at least partially rest on the implant body 22, insertion of the implant body 22 temporarily stops. At this point, the manipulating tool 40 (which in some embodiments manipulates only the ramped nose and in other embodiments also serves as an insertion tool to insert/advance the implant body 22) is used to slightly advance the ramped nose 34 separately from the implant body 22. As the ramped nose 34 is advanced, the proximal ends of the upper ramp 42 and the lower ramp 44 separate from the ramp notches 48, as shown in FIG. 6.

Either before or after advancing the ramped nose 34 to the position shown in FIG. 6, the ramped nose support 38 is at least partially withdrawn into the channel 36 (distally, or in the direction of the second end 32) until it no longer supports the upper ramp 42 and the lower ramp 44, as shown in FIG. 6. At this point, the upper ramp 42 and the lower ramp 44 collapse or are collapsed, as shown in FIG. 7. As discussed, in some embodiments, the collapse is caused by a biasing member of the ramped nose 34. In other embodiments, the collapse is caused by a collapsing force applied by the surgeon, such as through wires attached at the proximal ends of the upper ramp 42 and the lower ramp 44, or by a motion of the manipulating tool 40 (e.g., a rotation thereof).

The manipulating tool 40 is attached to any one of the upper ramp 42, the lower ramp 44, or the pin member 46, such that the surgeon can now apply a withdrawing force to the manipulating tool 40, withdrawing the collapsed ramped nose 34 into the channel 36, as shown in FIG. 8. In some embodiments, the ramped nose 34 remains in the channel 36 after implant, while in other embodiments, the ramped nose 34 is withdrawn from the implant 22 entirely.

Nevertheless, once the ramped nose 34 is withdrawn, the surgeon further inserts the implant 20 until the implant body 22 is fully within and properly positioned in the implant location. The surgeon then releases the implant body and either releases the ramped nose 34 within the channel or withdraws the ramped nose 34 with any insertion tool (and with the manipulating tool 40 and the ramped nose support 38).

In some alternative procedures, it is possible to fully place the implant body 22 before collapsing the ramped nose 34 and withdrawing the ramped nose 34 from its deployed position. Such procedures should be used with caution, however, to ensure that the ramped nose 34 does not cause damage to structures outside the implant location.

Figure 9:
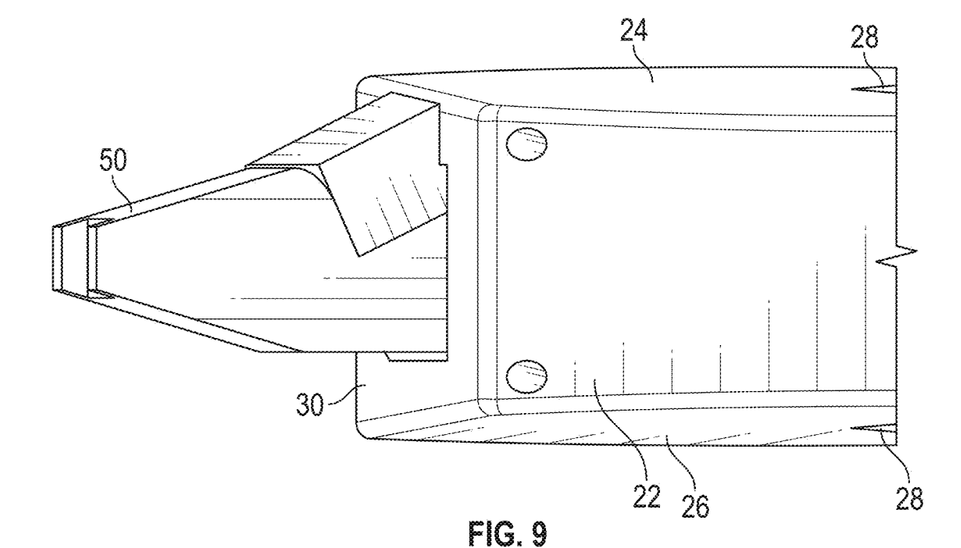
FIG. 9 shows a perspective view of a portion of another representative implant with a deployable nose.

While the ramped nose 34 of the embodiment illustrated with respect to FIGS. 4-8 expands in two dimensions (e.g., in the cranial-caudal direction) only, embodiments of the invention are not limited to such expansion. Accordingly, FIG. 9 shows an alternative ramped nose 50 having a capability to expand in additional directions (e.g., in both the cranial-caudal direction and the ventral-dorsal direction). Accordingly, the ramped nose 50 may deploy in multiple directions and collapse in multiple directions with an umbrella-like deployment/collapse.

In some embodiments, the ramps of the deployable ramped nose are attached to the implant body 22 and are configured to swing open with the help of a deployment tool that forces the ramps to swing open and deploy.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. An implantable medical device comprising:
an implant body having a length and a height; and
a deployable ramped nose comprising a pair of ramps adapted to selectively extend from the body and transition from a first height proximate the implant body to a second, shorter, height distal from the implant body;
wherein the ramps comprising proximal ends that rest on and engage with the implant body to prevent collapsing of the ramps; and
wherein the ramps are biased to a collapsed state such that when the deployable ramped nose is advanced while the implant body is retained against advancing, the proximal ends of the ramps disengage with the body and collapse to a position in which the deployable ramped nose may be withdrawn into the implant body.

2. The implantable medical device as recited in claim 1, wherein the deployable ramped nose is adapted to distract an implant site upon insertion of the implantable medical device.

3. The implantable medical device as recited in claim 1, wherein the deployable ramped nose is in a deployed state during initial insertion of the implantable medical device, and is retracted within the implant body after initial insertion of the implantable medical device.

4. The implantable medical device as recited in claim 1, wherein the deployable ramped nose is retracted before the implantable medical device is fully inserted, whereby the deployable ramped nose does not extend into a space beyond a targeted insertion location of the implant body during insertion of the implantable medical device.

5. The implantable medical device as recited in claim 1, wherein the pair of ramps are hingedly connected to an elongate member proximate a distal end of the deployable ramped nose.

6. The implantable medical device as recited in claim 5, wherein the proximal ends of the pair of ramps rest on and engage with a pair of shelves of the implant body to prevent collapsing of the ramps.

7. The implantable medical device as recited in claim 6, wherein when the deployable ramped nose is advanced while the implant body is retained against advancing, the proximal ends of the ramps disengage with the shelves and collapse to a position in which the deployable ramped nose may be withdrawn into the implant body.

8. The implantable medical device as recited in claim 1, wherein the implant body comprises a pair of shelves on which the proximal ends of the ramps rest on.

9. The implantable medical device as recited in claim 1, wherein the implant body comprises an intervertebral spacer.

10. The implantable medical device as recited in claim 1, wherein the deployable ramped nose is also adapted to transition from a first thickness proximate the implant body to a second, thinner, thickness distal from the implant body.

11. The implantable medical device as recited in claim 1, further comprising a tool adapted to selectively deploy the deployable ramp nose.

12. The implantable medical device as recited in claim 1, further comprising a tool adapted to selectively collapse and retract the deployable ramp nose.

13. A method for utilizing an implantable medical device having a deployable ramped nose, the implantable medical device comprising:
an implant body having a length and a height; and
a deployable ramped nose comprising a pair of ramps adapted to selectively extend from the body and transition from a first height proximate the implant body to a second, shorter, height distal from the implant body;
wherein the ramps comprising proximal ends that rest on and engage with the implant body to prevent collapsing of the ramps; and
wherein the ramps are biased to a collapsed state such that when the deployable ramped nose is advanced while the implant body is retained against advancing, the proximal ends of the ramps disengage with the body and collapse to a position in which the deployable ramped nose may be withdrawn into the implant body
wherein the method comprises:
deploying the deployable ramped nose from the implant body of the implantable medical device;
inserting the implantable medical device, with the deployable ramped nose leading, into an implant location, until the implant body is at least partially within the implant location; and
retracting the deployable ramped nose whereby the implantable medical device does not extend beyond the implant location but extends a full desired height of the implant body within the implant location.

14. The method as recited in claim 13, wherein the deployable ramped nose is retracted before the implant body is fully within the implant location.

15. The method as recited in claim 13, wherein the deployable ramped nose is retracted only after the implant body is fully within the implant location.

16. The method as recited in claim 13, wherein during the step of inserting the implantable medical device, the deployable ramped nose distracts the implant location to make room for the implant body.

17. The method as recited in claim 13, further comprising collapsing the deployable ramped nose before retracting the deployable ramp nose.

18. The method as recited in claim 13, further comprising removing the deployable ramped nose from the implant body after retracting the deployable ramped nose.

19. The method as recited in claim 13, further comprising disengaging a member that secures the deployable ramped nose against collapse and allowing the deployable ramped nose to collapse before retracting the deployable ramped nose.

20. The method as recited in claim 13, wherein a combination insertion/retraction tool is used to apply an advancing force to advance the implantable medical device into the implant location and to cause the deployable ramped nose to retract.

* * * * *